United States Patent [19]
Mikulich et al.

[11] Patent Number: 5,667,486
[45] Date of Patent: Sep. 16, 1997

[54] PROSTATIC STENT

[75] Inventors: Michael A. Mikulich, La Conversion; Claude O. Clerc, Morges; Michael R. Jedwab, Pully; Adrian Furrer, Morges; Alain Mariller, Pompaples, all of Switzerland; John H. Burton, Minnentonka; Claude Tihon, Eden Prairie, both of Minn.

[73] Assignee: AMS Medinvent, S.A., Crissier, Switzerland

[21] Appl. No.: 233,660

[22] Filed: Apr. 26, 1994

[30] Foreign Application Priority Data

Apr. 27, 1993 [SE] Sweden ............................ 9301415

[51] Int. Cl.$^6$ .............................. A61M 5/00; A61F 2/06; A61F 2/04
[52] U.S. Cl. ................................ 604/8; 623/1; 623/12; 606/195
[58] Field of Search .................. 604/8; 623/1, 12; 606/191, 195

[56] References Cited

U.S. PATENT DOCUMENTS

| 3,818,511 | 6/1974 | Goldberg et al. | 623/12 |
| 4,655,771 | 4/1987 | Wallsten | 623/1 |
| 4,822,333 | 4/1989 | Lavarenne | 623/12 |
| 4,955,859 | 9/1990 | Zilber | 604/8 |
| 4,973,301 | 11/1990 | Nissenkorn | 604/8 |
| 4,994,066 | 2/1991 | Voss | 606/108 |
| 5,059,169 | 10/1991 | Zilber | 604/8 |
| 5,061,275 | 10/1991 | Wallsten et al. | 623/1 |
| 5,269,802 | 12/1993 | Garber | 606/191 |
| 5,354,309 | 10/1994 | Schnepp-Pesch et al. | 606/198 |

FOREIGN PATENT DOCUMENTS

| 0183372 | 6/1986 | European Pat. Off. | A61M 29/00 |
| 323818 | 7/1989 | European Pat. Off. | A61F 2/04 |
| 2611486 | 9/1988 | France | A61F 2/04 |
| 4130431 | 3/1993 | Germany | A61F 2/04 |
| 1771719 | 10/1992 | Russian Federation | 623/12 |
| 2227175 | 7/1990 | United Kingdom | A61F 2/04 |
| WO8901798 | 3/1989 | WIPO | A61M 25/00 |
| WO9116005 | 10/1991 | WIPO | A61B 17/00 |

OTHER PUBLICATIONS

Kirby, R. and Christmas, T., Benign Prostatic Hyperplasia, 1993, Wolfe Publishing, pp. 63–71.

Primary Examiner—John G. Weiss
Assistant Examiner—Dennis Ruhl
Attorney, Agent, or Firm—Peter C. Richardson; Lawrence C. Akers; John L. LaPierre

[57] ABSTRACT

A prostatic stent and method of manufacture. The stent has an elongate body defining a passage therethrough and includes a distal section, a mid-section and a proximal section. The elongate body has a length sufficient to extend distally from a bladder neck to a position somewhat short of the external sphincter. The proximal section has a shape conforming to the neck of the urinary bladder.

13 Claims, 2 Drawing Sheets

FIG. 2
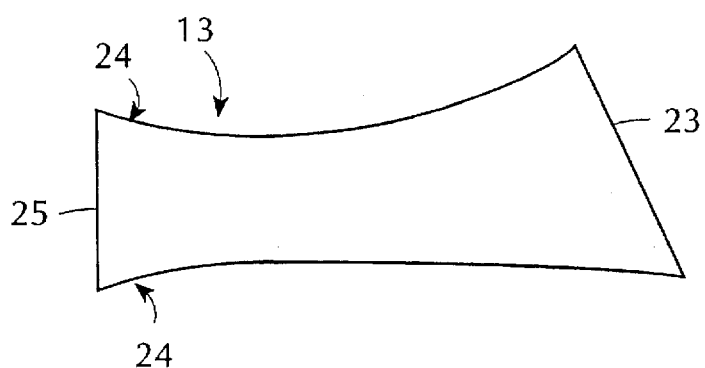
FIG. 3
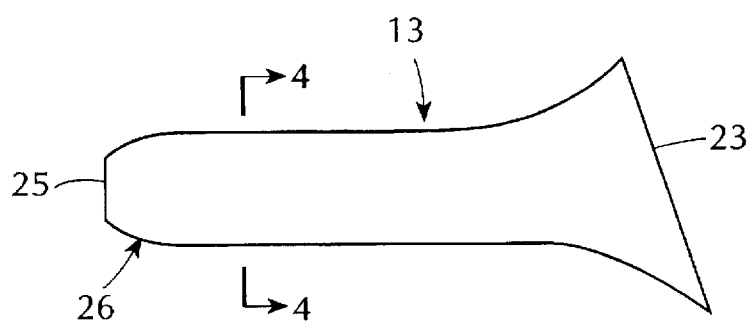
FIG. 4  FIG. 6
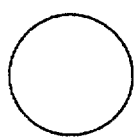 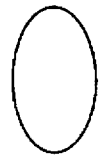
FIG. 5
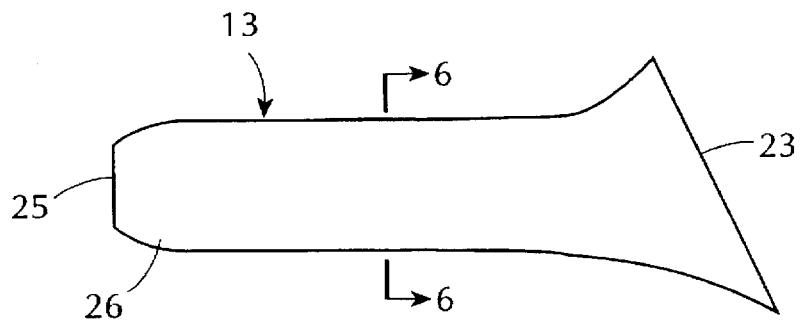

PROSTATIC STENT

BACKGROUND OF THE INVENTION

The present invention pertains to a prostatic stent and processes for the manufacture of such prostatic stent made of a metallic material. More specifically, the invention relates to a prostatic stent for non-surgical treatment of obstruction of the prostatic urethra, such as may arise in connection with benign prostatic hyperplasia or prostatic carcinoma.

A commonly occurring disorder in urology is the obstruction of the prostatic urethra. The disorder occurs in males due to enlargement of the prostatic gland, due either to hyperplasia or to cancer. A condition often found in older males is known as benign prostatic hyperplasia (BPH), and the condition can cause a plurality of inconvenient symptoms, such as difficulties in urination, strongly reduced capacity to urinate, and the condition may at times result in complete retention of urine which may lead to severe renal disorders.

The traditional procedure for treating problems associated with enlargement of the prostate gland has up to now been surgery constituted by cutting away interior sections of the prostate gland or complete surgical removal of the prostate. These are, however, procedures unfavored by many patients and there has been a search for alternative ways of dealing with the problem.

U.S. Pat. No. 5,059,169 is an example of such alternative to surgery. This patent discloses a prostatic stent provided with a conical flange disposed within the neck of the bladder, the opposite end of the stent body extending approximately to the verumontanum. The stent is provided with a textured exterior surface that frictionally engages the urethral walls to prevent migration of the stent into the bladder. Migration in the opposite direction is prevented by the conical flange.

However, this prior art high-friction prostatic stent has associated disadvantages, particularly at and around the conical flange disposed within the neck of the bladder due to the fact that the end of the stent does not conform to the bladder neck and in view of the fact that the proximal end of the stent is designed perpendicular to a center line of the body of the stent. This design means that the stent cannot be placed optimally to cover the complete bladder neck. Either it causes urinary stones (calculi, encrustation) to form on the device protruding into the bladder or the device does not completely cover the circumference of the bladder neck when the stent is placed further down the prostatic urethra. Thus, in using this device one runs the risk of not relieving the obstruction.

One object of the present invention is to provide an improved prostatic stent for the treatment of bladder outlet obstruction caused by an enlarged prostate.

Another object of the present invention is to provide a prostatic stent having a shape conformed to the neck of the urinary bladder to avoid urinary calculi or encrustation or to avoid uncovered areas of the prostatic urethra adjacent to the bladder neck.

Still another object of the invention is to provide a prostatic stent while avoiding migration of the stent into the bladder or distally towards the sphincter.

Yet another object of the invention is to provide processes for the manufacture of metallic braided prostatic stents showing improved performance when used for solving the problem of non-surgical management of bladder outlet obstruction.

Other objects and advantages of the present invention will be understood upon reading of the following disclosure taken together with the drawing and the appended claims.

SUMMARY OF THE INVENTION

The present invention is directed toward a prostatic stent having an elongate body defining a passage therethrough and comprising a distal section, a mid-section and a proximal section, with the elongate body having a length sufficient to extend distally from a bladder neck to a position somewhat short of an external sphincter, such as up to and/or passing the verumontanum, and with the proximal section having a shape conforming to the neck of the urinary bladder.

In order to conform to the neck of the urinary bladder it is preferred that the proximal end of the proximal section extends in a plane sloping at an angle to a normal to a center line of the body not exceeding about 50°. It is particularly preferred that the angle lies within the range of about 5° to about 40°, such as within a range of about 10° to about 30°.

In a preferred embodiment of the invention, the mid-section has a substantially constant cross-section along the mid section, namely the cross-section has a cross sectional area and shape that are substantially constant along the section.

In order that the proximal section shall have a shape conforming to the neck of the urinary bladder, it is preferably provided with a flare conforming to the tapered neck.

The prostatic stent of the invention can extend from the bladder neck to a position just short of the verumontanum and it can extend all the way up to somewhat short of the sphincter. It is, of course, important that the stent extends short of the sphincter so as not to interfere with the normal function of the sphincter. In embodiments where the stent extends to a position short of the sphincter and adjacent to the verumontanum, it is preferred that the body has a distally directed flare to prevent proximal migration of the stent thereby conforming to the surrounding urethral wall. On the other hand, in embodiments where the stent extends beyond the verumontanum and up to a position short of the sphincter, it is preferred that the body has a distally directed taper so as not to interfere with the sphincter function.

In the instant disclosure the term "distal" or "distally" refers to a direction from the insider of the patient body to the exterior thereof, whereas the term "proximal" or "proximally" refers to the opposite direction.

The prostatic stent according to the invention may have an approximately circular radial cross-section or it may have a non-circular radial cross-section for improved conformation to the surrounding urethral wall. In the latter case the non-circular radial cross-section may be of a flattened or oval shape.

It is preferred that the prostatic stent according to the invention is of a self-expandable type. Such stent is of the braided type comprising a flexible tubular body which has a diameter that is variable by axial movement of the ends of the body relative to each other and which is composed of several individual rigid but flexible thread elements each of which extends in helix configuration with the center line of the body as a common axis, a number of elements having the same direction of winding but being axially displaced relative to each other crossing a number of elements also axially displaced relative to each other but having the opposite direction of winding.

In a particularly preferred embodiment of such prostatic stent, the proximal end of the body extends in the plane that is substantially parallel to the oppositely extending filaments in the stent.

A further embodiment of the invention resides in a prostatic stent having an elongate body defining a passage therethrough, and comprising a proximal section having a flaring and oblique proximal end conforming both radially and axially to the walls of the surrounding bladder neck, further comprising a mid-section having a substantially constant cross-section along the mid-section, and a distal section, with the elongate body having a length sufficient to extend distally from a bladder neck to a position somewhat short of the external sphincter.

The invention also includes a process for the manufacture of a metallic braided prostatic stent, with the process comprising the steps:

a) preparing a braided hollow, deformable body of flexible filaments braided in an extended helix configuration having substantially straight cylindrical walls;

b) mounting the body resulting from step a) onto a mandrel with a shape corresponding to the desired shape of the finished stent;

c) applying energy or external pressure or both onto the body positioned on the mandrel to cause the body to conform to the shape of the mandrel;

d) removing the thus shaped body from the mandrel; and e) cutting the body to a desired length.

In an alternative embodiment of the foregoing process, steps b) through e) are replaced by the steps of:

b) mounting the body of step a) onto an articulated mandrel having a fixed arm and a mobile arm, with the mobile arm being positioned at an angle relative to the fixed arm;

c) applying energy to the body of step b) placed on the mandrel to cause the body to conform to the shape of the mandrel;

d) cutting the proximal section at an angle perpendicular to an axis of the mobile arm to obtain the oblique proximal end; and e) removing the body from the mandrel.

In an alternative process of the invention for the manufacture of a metallic braided prostatic stent the steps involved are:

a) providing a braiding bar with a shape corresponding to the shape of the finished stent;

b) preparing a braided body by performing the braiding of metallic filaments on the braiding bar;

c) removing the braided body from the braiding bar, optionally after the application of energy and/or pressure to the body while placed on the bar; and d) cutting the body to a desired length.

In yet an alternative process of the invention for the manufacture of a metallic braided prostatic stent, the process comprises the steps:

a) providing a braiding bar, the radial cross-section of which is substantially constant along its entire length;

b) preparing a braided body by performing the braiding at varying axial speed of the braiding bar to obtain a varying angle between the crossing filaments along the bar;

c) mounting the body resulting from step b) onto a mandrel with a shape corresponding to the desired shape of the finished stent;

d) applying energy and/or pressure to the body when placed on said mandrel to cause the body to conform to the shape of the mandrel, e) removing the thus shaped body from the mandrel; and f) cutting the shaped body to a desired length.

BRIEF DESCRIPTION OF THE DRAWINGS

Drawing

FIG. 2 is a schematic view of a stent like that depicted in FIG. 1 but illustrating a stent having a distal flare.

FIG. 3 is a schematic view of a stent like that depicted in FIG. 1 but illustrating a stent having a distal taper.

FIG. 4 is a cross sectional view of the stent taken along line 4—4 of FIG. 3.

FIG. 5 is a schematic view of a stent like that depicted in FIG. 3.

FIG. 6 is a cross sectional view of the stent taken along line 6—6 of FIG. 5.

DETAILED DESCRIPTION OF THE PREFERRED EMBODIMENTS

Figure 1:
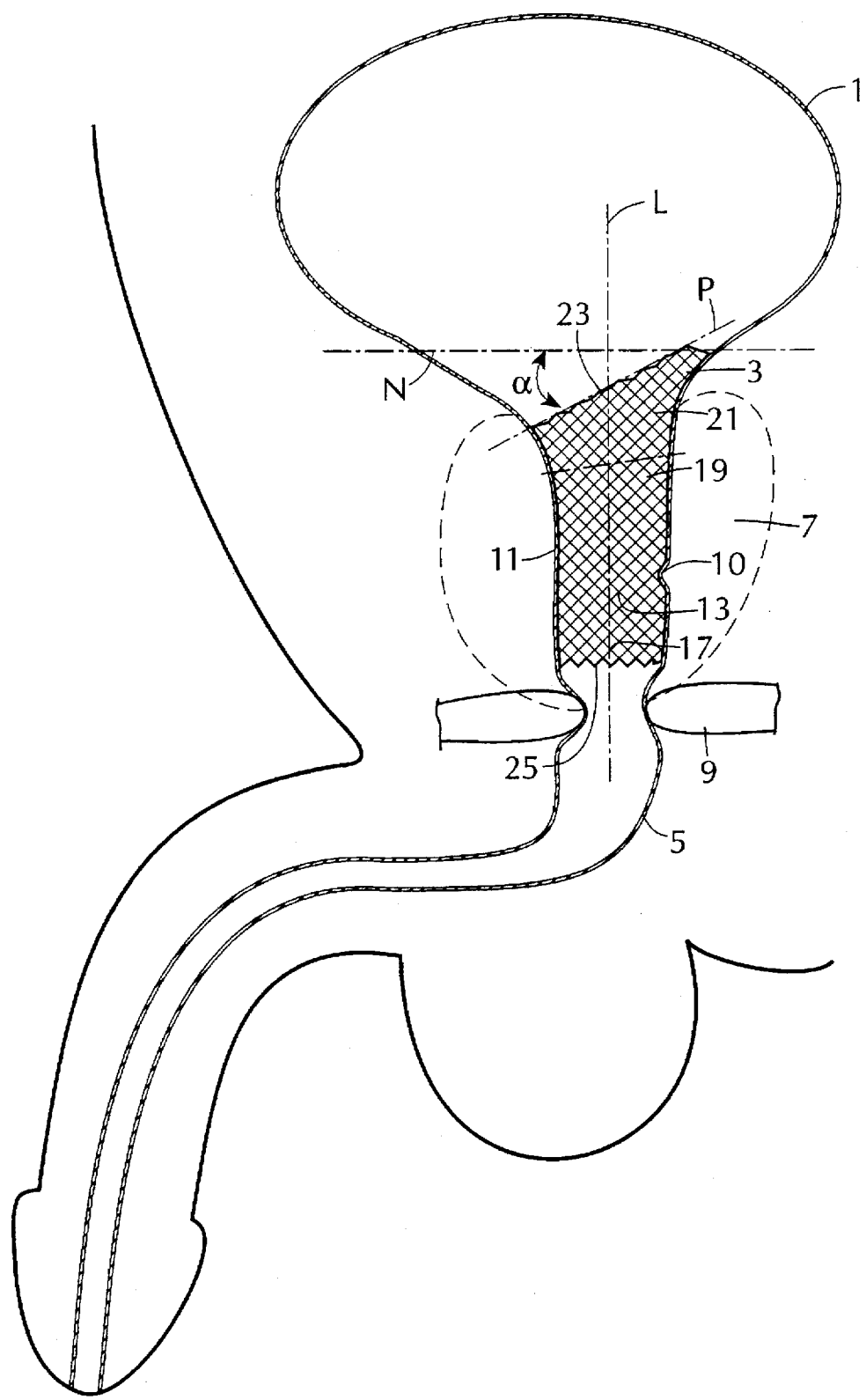
FIG. 1 is a schematic perspective view in cross-section in a sagittal plane showing the urinary tract and bladder and the prostatic stent according to the invention in an implanted position within the urethral tract.

With reference to the drawing there is shown in a diagrammatic manner a cross-section in a sagittal plane of the area surrounding the urinary tract including the bladder. In the drawing there is shown the bladder 1 having a tapered neck 3. The bladder neck 3 tapers into the urethra 5, and the prostatic part 11 of the urethra 5, approximately 3 to 4 cm thereof, is surrounded by the prostate gland 7. In the drawing there is also diagrammatically shown the external sphincter 9, whose normal function is to keep the urethra closed until urination when it opens for emptying the bladder 1. On the rear wall of the urethra 5 (more particularly the upper portion 11 thereof) there is a small projection, the verumontanum 10.

Shown in an implanted position in the upper part of urethra 5 is a stent 13 placed or located in accordance with the invention. Sections 17, 19, 21 form an elongate body 13 constituting the stent proper. A center line L through the elongate body 13 is shown in the drawing.

The embodiment of the stent 13 shown in the drawing is designed in accordance with the prosthesis for transluminal implantation disclosed in U.S. Pat. No. 4,655,771, which patent is incorporated herein by reference. For details regarding this type of stent, reference is made to the disclosure of the U.S. Pat. No. 4,655,771. It is preferred that the stent is made of a material possessing springiness or agility combined with suitable elasticity. A preferred material is a medicinally acceptable metal, for example Phynox, Elgiloy, MP35N or titanium.

The stent has a proximal end 23 and a distal end 25. The proximal end 23 of stent 13 is designed to conform to the neck 3 of the urinary bladder 1. As shown in the drawing, the plane P of the proximal end 23 of stent 13 has a sloping extension under an angle α to the normal N to the center line L of the elongate stent body. This sloping extension of proximal end 23 results in a stent configuration closely conforming to the surrounding neck 3 of bladder 1 resulting in advantages to be explained below.

In the embodiment shown in the drawing, the distal end 25 and distal section 17 of stent 13 extend to a position short of sphincter 9 and the distal section has a distally directed taper so as not to interfere with the sphincter function. The distal section 17 of the stent may also extend to a position somewhat short of the verumontanum 10 and is then preferably provided with a distally directed flare 24 near distal end 25 of stent 13 (FIG. 2) for the purpose of preventing proximal migration of the stent and also to conform to the surrounding urethral wall. Where the stunt extends beyond the verumontanum and up to a position short of the sphincter, it is preferred that the stent has a distally directed taper 26 (FIG. 3) so as not to interfere with the sphincter function. The stent may have an approximately circular radial cross-section as shown in FIG. 4 or it may have a non-circular radial cross-section, namely a flattened or oval shape such as that depicted in FIG. 5–6.

The procedure for preparing for implantation and the implantation proper will now be described in some detail.

In order to select the correct size of the prostatic stent the urologist determines the length of the prostatic urethra. The length of the prostatic urethra from the bladder neck to the verumontanum or to the sphincter, respectively, can be determined by using a measuring catheter. The measure taken up to this point are largely conventional to the skilled urologist.

After selection of the appropriate stent size due consideration being taken of the fact that the stent must be shorter than the measured length of the prostatic urethra to allow for the natural elongation of the stent in response to the pressure of the enclosing urethral walls, the prostatic stent applied to a suitable delivery instrument is then inserted into the prostatic urethra via the penis and the urethral tract to the position shown in the drawing. It is important to note that the sloping end 23 of the stent 13 has the orientation shown in the drawing, i.e. the slope being directed to be at a maximum in the direction of the sagittal plane through the center line L of the stent body 13.

It is important to note that the prostatic stent does not extend into the external sphincter because such position of the stent will cause incontinence to the patient. After proper positioning of the stent, the stent is released from the implantation instrument, and the instrument is withdrawn and removed from the patient.

The feature of the proximal section 21 of the stent 13 being designed with a shape conforming to the neck 3 of the urinary bladder 1 results in important advantages in practical use of the stent. Thus, as is understood from the drawing, the conformed shape of the proximal end 23 of the proximal section 21 of stent 13 means that urinary calculi or encrustation cannot accumulate on the stent due to the fact that it fits snugly to the interior of the neck 3 of bladder 1 and becomes covered with tissues after implantation. Nor will there be uncovered parts on the other side of the stent. The stent will perform its opening and supporting functions all the way to the entire bladder neck without allowing wires to protrude into the bladder which could become calcified. Furthermore, the proximal flare of the proximal section 21 of the stent prevents the stent from distal migration towards the sphincter 9. On the other hand, in embodiments where the distal section 17 of the stent has a distally directed flare proximal migration of the stent into the bladder will be prevented.

It is to be noted that the invention is not to be limited to the exact details of constructional features or other aspects as shown and described, as obvious modifications of equivalence will be apparent to the skilled artisan, and the invention is therefore to be limited only by the scope of the appended claims.

We claim:

1. A prostatic stent comprising an elongate body having a proximal end, a distal end and a passageway extending therebetween and including a distal section, a mid-section and a proximal section, with said elongate body being of a length sufficient to extend from a urinary bladder neck defining a shape to a position proximally of an external sphincter, said distal section having a distally directed flare adapted to conform to a surrounding urethral wall and to prevent proximal migration of the stent, said proximal section having a first terminus with said proximal end being the first terminus of said proximal section and extending in a plane sloping at an angle $\alpha$ of not more than about 50° to a normal to a central axis of said body, with the slope of said proximal end being such that the proximal end is configured to conform to said neck and adapted to be closely received within the entrance to the bladder and with said proximal section being elastic and being sized and configured and adapted to substantially conform to the shape of said neck.

2. The stent according to claim 1 wherein said angle $\alpha$ lies within a range of from about 5° to about 40°.

3. The stent according to claim 2 wherein said angle $\alpha$ lies within a range of from about 10° to about 30°.

4. The sent according to claim 1 wherein said mid-section has a substantially constant cross-section along the mid-section, the cross-section having a cross sectional area and shape substantially constant along the mid-section.

5. The stent according to claim 1 wherein said elongate body is substantially circular in cross section.

6. The stent according to claim 5 wherein said elongate body is non-circular in cross section.

7. The stent according to claim 6 wherein said non-circular cross section is an oval configuration.

8. The stent according to claim 1 wherein said body is self-expandable.

9. The stent according to claim 8 wherein said body comprises braided filaments.

10. A prostatic stent comprising an elongate body having a wall structure defining a passage therethrough, said body being formed of braided filaments and with said wall having openings between said braided filaments, said body further comprising a proximal section including a flared and oblique proximal end adapted to conform both radially and axially to an inner surface of a surrounding bladder neck, a mid-section having a substantially constant cross-section with a cross sectional area and shape being substantially constant along the mid-section, and a distal section having a distally directed flare adapted to conform to a surrounding urethral wall and to prevent proximal migration of the stent, said elongate body having a length sufficient to extend distally from said bladder neck to a position proximally of an external sphincter, said wall being adapted to enable growth of natural tissue into said stent.

11. The stent according to claim 10 wherein said body is self-expandable.

12. A prostatic stent comprising an elongate body having a proximal end, a distal end and a passageway extending therebetween and including a distal section, a mid-section and a proximal section, with said elongate body being of a length sufficient to extend from a urinary bladder neck defining a shape to a position proximally of an external sphincter, said distal section having a distally directed taper so that the stent does not interfere with said external sphincter, said proximal section having a first terminus with said proximal end being the first terminus of said proximal section and extending in a plane sloping at an angle $\alpha$ of not more than about 50° to a normal to a central axis of said body, with the slope of said proximal end being such that the proximal end is configured to conform to said neck and adapted to be closely received within the entrance to the bladder and with said proximal section being elastic and being sized and configured and adapted to substantially conform to the shape of said neck.

13. A prostatic stent comprising an elongate body defining a passage therethrough, a proximal section including a flared and oblique proximal end, with each said proximal section and said proximal end being configured and adapted to closely conform both radially and axially to fit snugly to an inner surface of a surrounding bladder neck, said proximal end extending in a plane sloping at an angle $\alpha$ to a normal to a central axis of said body, a not exceeding about 50° and being such that the proximal end is adapted to be received within the entrance to the bladder, a mid-section having a substantially constant cross section along a length and a distal section having a distally directed flare adapted to conform to a surrounding urethral wall and to prevent proximal migration of the stent, said body comprising braided filaments with said elongate body having a length sufficient to extend distally from said bladder neck to a position proximally of an external sphincter.

* * * * *